(12) United States Patent
Phanstiel, IV (10) Patent No.: US 9,285,320 B2
(45) Date of Patent: *Mar. 15, 2016

(54) FLUORESCENT CYTOTOXIC COMPOUNDS SPECIFIC FOR THE CELLULAR POLYAMINE TRANSPORT SYSTEM

(71) Applicant: University of Central Florida Research Foundation, Inc., Orlando, FL (US)

(72) Inventor: Otto Phanstiel, IV, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/835,708

(22) Filed: Mar. 15, 2013

(65) Prior Publication Data
US 2013/0337494 A1    Dec. 19, 2013

Related U.S. Application Data

(63) Continuation-in-part of application No. 12/754,962, filed on Apr. 6, 2010, now Pat. No. 8,410,311, and a continuation-in-part of application No. 12/113,540, filed on May 1, 2008, now Pat. No. 8,497,398.

(60) Provisional application No. 60/166,889, filed on Apr. 6, 2009.

(51) Int. Cl.
| | |
|---|---|
| C07C 211/00 | (2006.01) |
| A01N 33/18 | (2006.01) |
| A01N 33/24 | (2006.01) |
| A61K 31/04 | (2006.01) |
| G01N 21/64 | (2006.01) |
| C07C 255/58 | (2006.01) |
| G01N 33/50 | (2006.01) |
| G01N 33/533 | (2006.01) |
| G01N 33/574 | (2006.01) |
| G01N 33/58 | (2006.01) |

(52) U.S. Cl.
CPC .......... *G01N 21/6486* (2013.01); *C07C 255/58* (2013.01); *G01N 33/5008* (2013.01); *G01N 33/533* (2013.01); *G01N 33/574* (2013.01); *G01N 33/582* (2013.01); *C07C 2103/24* (2013.01)

(58) Field of Classification Search
CPC .......................... C07C 2103/24; G01N 33/574
See application file for complete search history.

(56) References Cited

U.S. PATENT DOCUMENTS

| | | | |
|---|---|---|---|
| 6,172,261 B1 * | 1/2001 | Vermeulin et al. | 506/15 |
| 7,001,925 B1 | 2/2006 | Phanstiel | |
| 8,410,311 B1 * | 4/2013 | Phanstiel, IV | 564/305 |

OTHER PUBLICATIONS

Palmer et al. Amino Acids (2010) 38; 415-422.*
Gardner, Richard Andrew et al., "N1-Substituent Effects in the Selective Delivery of Polyamine Conjugates into Cells Containing Active Polyamine Transporters", J. Med. Chem., 2004, vol. 47, pp. 6055-6069.
Kaur, Navneet et al., "A Comparison of Chloroambucil- and Xylene-Containing Polyamines Leads to Improved Ligands for Accessing the Polyamine Transport System", J. Med. Chem., 2008, vol. 51, pp. 1393-1401.
Wang, C. et al., "Synthesis and Biological Evaluation of N1-(anthracen-9-ylmethyl)triamines as Molecular Recognition Elements for the Polyamine Transporter," J. Med. Chem., 2003, vol. 46, pp. 2663-2671.
Petros, L. et al., "Polyamine Analogs with Xylene Rings Induce Antizyme Frameshifting, Reduce ODC Activity, and Deplete Cellular Polyamines", J. Biochem., 2006, vol. 140, pp. 657-666.

* cited by examiner

*Primary Examiner* — Clinton Brooks
(74) *Attorney, Agent, or Firm* — Timothy H. Van Dyke; Beusse, Wolter, Sanks & Maire, PLLC (57) ABSTRACT

Cyano-substituted anthracene containing polyamines were synthesized and shown to be efficient polyamine transporter ligands. Moreover, these compounds (3 and 4) had improved fluorescence properties over previously known anthryl-polyamine conjugates, which facilitated their intracellular trafficking by confocal microscopy and fluorescence methods. These cytotoxic fluorescent agents may find use as molecular probes which traffic into cells via the polyamine transport system and may also be viable anticancer drugs which are readily quantified in human tissues due to their excellent fluorescence properties: (excitation: λ 405 nm) and emission (420 nm) occurs in the visible light range. The ability to excite and emit in the visible range provides an advantage to these probes as these wavelengths are considered non-toxic to human cells (versus ultraviolet mediated excitations, λ<400 nm) and visible light lasers are less costly to purchase and operate than UV laser sources.

18 Claims, 6 Drawing Sheets

REACTION SCHEME 3

FIG. 4

REACTION SCHEME 4

FIG. 5

FIG. 6

FLUORESCENT CYTOTOXIC COMPOUNDS SPECIFIC FOR THE CELLULAR POLYAMINE TRANSPORT SYSTEM

CROSS REFERENCE TO RELATED APPLICATIONS

This application is a continuation-in-part of U.S. application Ser. No. 12/754,962, filed 6 Apr. 2010, which claimed priority to U.S. Provisional Application Ser. No. 60/166,889, filed on 6 Apr. 2009, and which also was a continuation-in-part of U.S. application Ser. No. 12/113,540, filed on 1 May 2008, the entirety of each application referenced above is incorporated by reference herein in its entirety.

FIELD OF THE INVENTION

The present invention relates to the field of mammalian cellular physiology and, more particularly, to fluorescent molecules that are transported into a cell via the polyamine transport system.

BACKGROUND OF THE INVENTION

Polyamines are organic compounds having at least two primary amine groups, for example R—$NH_2$. These compounds have a role in the metabolism of mammalian cells, translation, transcription and chromatin remodeling as well as the construction of the eukaryotic initiation factor eIF-5A. The polyamines play diverse roles within cells and many of their exact functions are not well described. It is known that cells can biosynthesize polyamines and that, if cellular polyamine biosynthesis is blocked, exogenously supplied polyamines may be imported into the cell via the so called polyamine transporter system (PTS).

Polyamines are synthesized in cells through highly regulated pathways, and maintaining cellular polyamine homeostasis is achieved through a balance of synthesis, degradation and import. They exist as polycations at physiological pH and are known to bind to DNA and other nucleic acids. In structure, they are aliphatic amines and at physiologic pH exist as polycations, where the cationic charges are found at regularly spaced intervals (unlike, say, $Mg^{++}$ or $Ca^{++}$, which are isolated point charges). In summary, polyamines are essential growth factors that cells require for proper growth and development.

When synthesis of cellular polyamines is inhibited, the cell's growth is also inhibited. Addition of exogenous polyamines to the extracellular milieu reactivates the growth of these cells. Most eukaryotic cells have a polyamine transporter system on their cell membrane that facilitates the import of exogenous polyamines. The polyamine transporter system (PTS) is highly active in rapidly proliferating cells and is the target of some chemotherapeutics currently under development. The current belief in the field is that cancer cells are unable to synthesize sufficient polyamines to sustain their rapid growth rates. Since many cancer cell lines have active polyamine transporters, it is possible to selectively target these cells via their need for polyamine growth factors and their active polyamine transport systems.

SUMMARY OF THE INVENTION

With the foregoing in mind, the present invention advantageously provides novel fluorescent compounds that are rapidly internalized by a cell via the polyamine transporter system, thus providing easily tracked probes for the further study of this important transport mechanism. Consequently, it may be possible to attach a therapeutic drug moiety to the presently disclosed fluorescent PTS probes to provide the unique ability of tracking the drug into the cell by visualizing the fluorescent tag.

Figure 1:
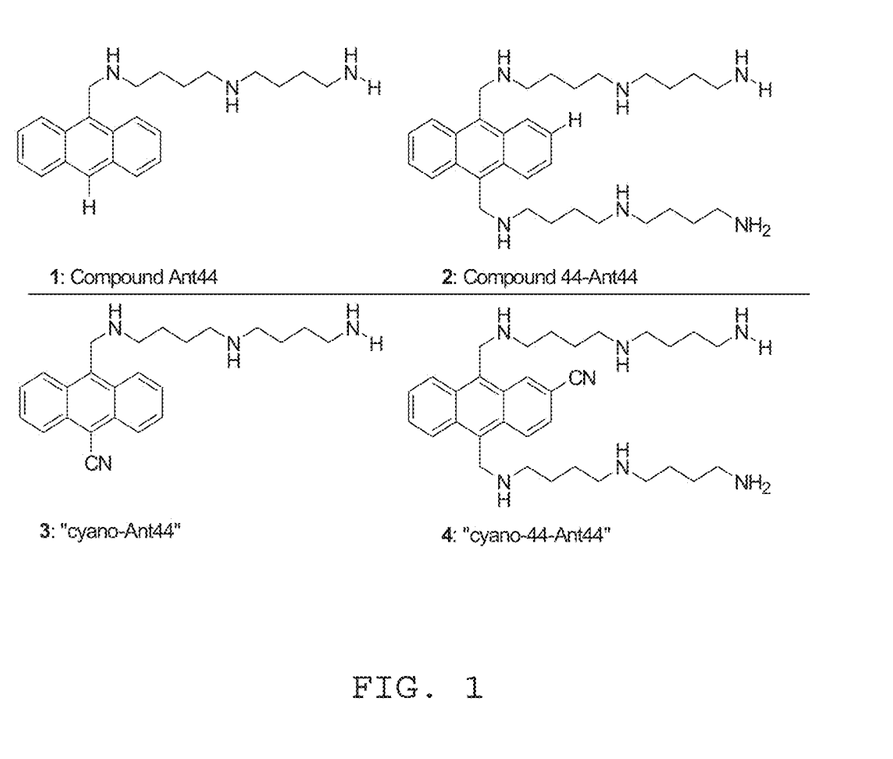
FIG. 1 provides the formulas for previously known compounds 1-2, as well as presently disclosed novel compounds 3-4 according to an embodiment of the present invention.

After studying polyamine transport processes for many years, we discovered and have previously disclosed compounds 1 and 2 as optimal polyamine transporter selective agents (FIG. 1). These compounds enter and kill cells via their polyamine transport system. The polyamine transport system is a measurable phenomenon, but the genes and proteins involved are poorly understood. As such there are few molecular biomarkers that one can measure to assess the polyamine transport activity of cells. In one aspect, the instant invention provides compounds 3 and 4, which are highly fluorescent compounds useful for tracking polyamine uptake processes in mammalian systems (FIG. 1). In another aspect, there is provided a plurality of methods that enable the identification, monitoring and quantification if desired of the PAT activity of a cell.

We have synthesized these fluorescent probes (compounds 3 and 4) and have performed confocal microscopy with compound 3 to illustrate this technology in action. An important improvement over earlier systems is that even though compounds 1 and 2 are PTS-selective and fluorescent, they require excitation in the ultraviolet range (393 nm) and emit in the visible range (410 nm). This requirement is detrimental to biological studies as the UV radiation is injurious and can kill the exposed cells.

Critically, new compounds 3 and 4 contain a cyano group, which extends the compounds' pi system sufficiently so that these systems are now excited at wavelengths of at least 400 nm, e.g., 405 nm (blue light), above the blue light range and emit in the visible light range, for example, at 420 nm. This improvement in their photophysical properties coupled with their high selectivity in entering cells via the PTS make these compounds valuable new tools for molecular and cell biologists interested in tracking polyamine uptake phenomena via fluorescence measurements or via confocal microscopy.

The present disclosure also contemplates that the invention includes compounds 3 and 4 in a pharmaceutical composition acceptable for administration to a patient. Those skilled in the art should recognize that the compounds of this invention may be administered to mammals, preferably humans, either alone or in combination with pharmaceutically acceptable carriers, excipients or diluents, in a pharmaceutical composition, according to standard pharmaceutical practice. The compounds can be administered by any route but are preferably administered parenterally, including by intravenous, intramuscular, intraperitoneal, subcutaneous, rectal and also by topical routes of administration.

As used herein, the term "composition" is intended to encompass a product comprising the disclosed compounds in amounts effective for causing the desired effect in the patient, as well as any product which results, directly or indirectly, from combination of the specific ingredients. However, the skilled should understand that when a composition according to this invention is administered to a human subject, the daily dosage of active agents will normally be determined by the prescribing physician with the dosage generally varying according to the age, weight, sex and response of the individual patient, as well as the severity of the patient's symptoms.

As used herein, the terms "pharmaceutical composition" and "pharmaceutically and/or pharmacologically acceptable compositions" for administration to a patient refer to molecular entities and/or compositions that do not produce an adverse, allergic and/or other untoward reaction when administered to a subject, be it animal or human, as appropriate. As known to the skilled, a pharmaceutically acceptable composition or carrier includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated. Supplementary active ingredients can also be incorporated into the compositions. For administration, preparations should meet sterility, pyrogenicity, general safety and/or purity standards as required by FDA Office of Biologics standards. The skilled will find additional guidance in preparation of pharmaceutically acceptable compositions by consulting United States Pharmacopeia (USP) or other similar treatises employed in the pharmaceutical industry.

In another aspect, the present disclosure also contemplates a second compound, of Formula 4 and related to the compound of Formula 3 by both being derivatives of an anthracene compound. This second compound is shown below according to Formula 4 and salts thereof. The compound of Formula 4 has chemical and biological properties that parallel those of the compound of Formula 3 and may be employed in a likewise manner, as described above.

As used herein, the terms "treat," "treating" or "method of treatment" refer to both therapeutic treatment and prophylactic or preventive measures, wherein the object is to prevent or slow down (lessen) an undesired physiological change or disorder, such as the development or spread of cancer or other proliferation disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, treatment with a compound of the invention may include reduction of undesirable cell proliferation, and/or induction of apoptosis and cytotoxicity. "Treatment" can also mean prolonging survival as compared to expected survival if not receiving treatment.

The terms "effective to inhibit" or "growth inhibitory amount" of the compounds of the invention refer to an amount which reduces (i.e., slows to some extent and preferably stops) proliferation of a target cell, such as a tumor cell, either in vitro or in vivo, irrespective of the mechanism by which cell growth is inhibited (e.g., by cytostatic properties, cytotoxic properties, etc.).

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE INVENTION

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, and other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

U.S. patent application Ser. No. 12/113,540 was filed on 1 May 2008 and application Ser. No. 12/113,970 was filed on 2 May 2008. These two applications disclosed other polyamine compounds related to and having similar biological properties to the presently disclosed compounds 3 and 4. Accordingly, these two patent applications are incorporated herein by reference in their entireties.

In the present disclosure, using Chinese hamster ovary (CHO) cells as a test cell line, we have shown that compound 3 is significantly more toxic to wild type CHO cells than to their CHOMG mutant, which is defective in polyamine transport. Since these compounds use the PTS for cellular entry, they are very toxic to cell lines containing active polyamine transporters (e.g., CHO cells) but less so to cell lines with defects in this pathway (CHOMG).

As known to those skilled in the art, the IC$_{50}$ is the concentration of the drug required to kill 50% of the relative cell population. That is, the lower the IC$_{50}$ value, the more potent the drug. See Table 1. We employed confocal microscopy to look at the cell localization behavior of compound 3 in these two cell lines at different time points.

Figure 2:
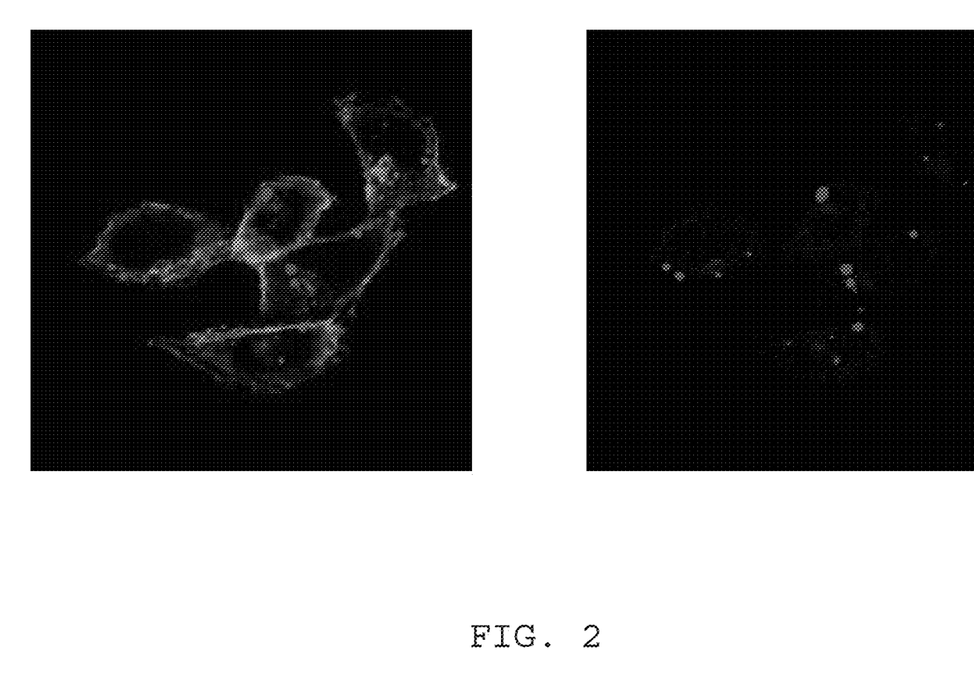
FIG. 2 shows a fluorescence microscopy view of polyamine transport inactive CHOMG cells treated with compound 3 (10 µM) after 4 hours.

FIG. 2 shows inactive CHOMG cells treated with compound 3 (10 µM), the fluorescence microscopy view being taken after the cells had been exposed to the compound for 4 hours. Compound 3 is mainly sequestered in intracellular vesicles at the 4 hr incubation time point (FIG. 2). The CHOMG mutant defect seems to block vesicular escape of the probe. Note that the fluorescent probe, compound 3, appears as a blue dot (right image) as it remains localized within these large spheroid bodies. The green image (left image) is acquired from an actin-binding stain to show the cells' cytoskeletal architecture surrounding the blue probe 3.

Figure 3:
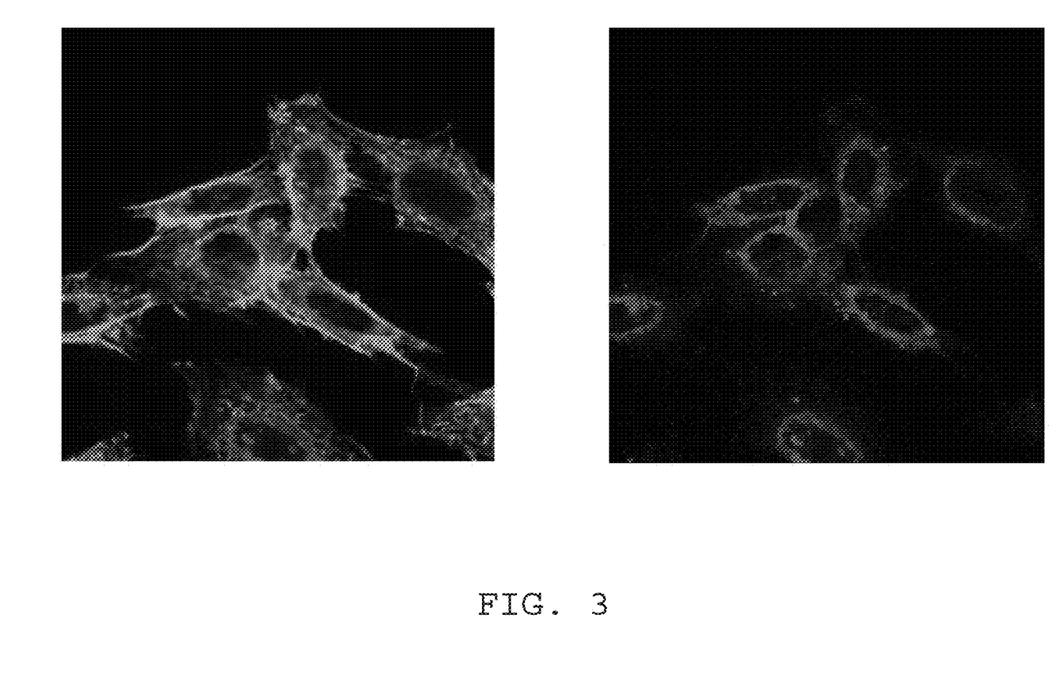
FIG. 3 shows a fluorescence microscopy view of polyamine transport-active CHO wild type cells treated with compound 3 (10 µM) after 4 hours.

In FIG. 3, polyamine transport-active CHO wild type cells are shown after being treated with compound 3 (10 μM) for 4 hrs. In contrast to CHOMG, shown in FIG. 2, the wild type CHO cells shown in FIG. 3 allow compound 3 to escape/avoid the spheroidal compartments and arrive at the perinuclear compartment after 4 hrs. of incubation. This is clearly seen as the 'blue halo' effect. Note that the fluorescent drug, compound 3, appears as a blue image. The green image is taken with an actin-binding stain to show the cells' cytoskeletal architecture.

The skilled artisan will recognize that the CHOMG/CHO $IC_{50}$ ratio is indicative of PTS selectivity. As seen in Table 1, control compound 5 (a water soluble anthracene derivative with the incorrect message to utilize the polyamine transporter) gave the same $IC_{50}$ value in both the CHO and CHOMG cell lines, i.e. the CHOMG/CHO $IC_{50}$ ratio=1. Therefore, the control compound 5 had no selectivity for targeting cells with the active PTS. In contrast, the smart polyamine probes 1-4 all showed greater toxicity to the CHO cell line over its CHOMG mutant ($IC_{50}$ ratios>>1). In addition, the L1210 cells (murine leukemia cells) were more sensitive (lower $IC_{50}$ values) to the smart probes 1-4 than the control 5. These cells also gave lower $K_i$ values, which is indicative of greater binding to the putative polyamine transporter. In contrast the control 5 gave a significantly higher $K_i$ value (32.2 μM).

Figure 6:
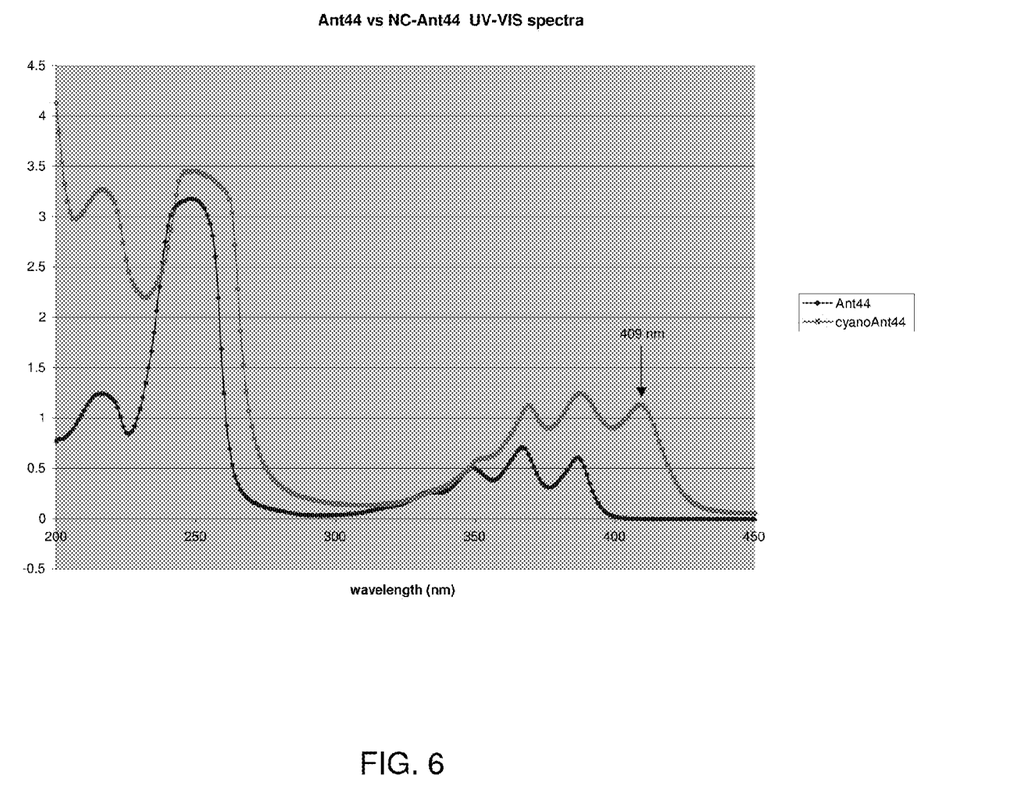
FIG. 6 shows a line graph depicting the UV-VIS spectra of Ant44 (compound 1) and cyanoAnt44 (compound 3) in PBS buffer, 100 µM at 25° C.

A comparison of the UV-visible absorbance spectra of the Ant44 (compound 1) and cyanoAnt44 (compound 3) derivatives (FIG. 6) shows a shift to longer wavelength (red shift) of the absorbance spectrum upon cyanation of the anthryl ring. The extended pi system is responsible for this shift to 409 nm and was part of the design process in constructing the cyano derivative.

An important reason for using >400 nm for polyamine probe excitation is that one can use a visible light laser, for example a blue laser, to excite the compound at 405 nm. In contrast, exciting probes of wavelength below 400 nm would require a very costly UV laser, which are also expensive to maintain and to cool during operation.

In addition, UV excitation has other problems since other biofluorophores such as DNA bases, tryptophan, etc., can be excited by UV radiation. Accordingly, in order to distinguish the presently disclosed polyamine probes it was advantageous to be able to use excitation frequencies in the visible light region. We accomplished this by making the cyano derivatives which have an absorption band near 409 nm in phosphate buffered saline (PBS) (see FIG. 6).

Numerous methods are contemplated herein for advantageously utilizing the novel compounds. The methods include but are not limited to use of the compounds in screening methods, including high throughput screening methods, to identify particular cellular targets, to better understand cellular polyamine transport activity in cells, and to track the uptake and localization of therapeutic agents into a cell. It is understood that the techniques described herein in one method may also be utilized in any other method as described herein.

In one embodiment, there is provided a method for screening for cells that may be susceptible to a polyamine transport system (PTS) targeting strategy. The method comprises contacting at least one test cell with a fluorescent cyano-substituted anthracene probe; incubating the cells for a time sufficient for the probe to enter the cell; optionally washing the test cell to remove unbound probe; exciting the probe using a visible light source; and determining whether the probe is internalized by the test cell. A test cell that internalizes the probe is identified as a cell that is susceptible to a polyamine transport system targeting strategy.

In one embodiment, the test cells are cancerous cells from one or more known cancerous cell lines. In this way, the described methods may identify one or more cancers that strongly rely on the PTS for their growth. Suitable therapies, such as therapeutic agents which show high selectivity for the PTS, may then be developed and/or administered to the subjects having that type of cancer.

In another embodiment, the steps are carried out on one or more biopsy samples taken from a tumor of a subject. In this way, the methods described herein may be utilized to determine the extent to which cells of the tumor are utilizing the PTS for their growth. Suitable therapies may then be provided to the subject in response to the detected PTS activity of the cell. For example, a high usage of the PTS may allow for increased dosing with a PTS targeting anticancer therapy.

The fluorescent cyano-substituted anthracene probe may be any fluorescent cyano-substituted anthracene compound. In one embodiment, the fluorescent cyano-substituted anthracene probe comprises at least one of compound 3 or compound 4.

Typically, the contacting is done under physiological conditions, such as in PBS buffer at 25° C. The concentration of probe in the medium may be any suitable concentration, such as from 1-100 μM. The incubation time for the medium may be determined by routine experimentation to determine when the probe has had sufficient time to enter the cell. In certain embodiments, the incubation time may be from 2-6 hours, for example. Optionally, the method includes washing the cells with a suitable medium, such as phosphate buffer saline (PBS).

After the incubation and washing steps, the probe may be excited using a visible light source. As noted above, a critical advantage of compounds described herein, such as compounds 3 and 4 is that they may be excited in the visible light range and thus the detection of the compounds does not adversely affect the cells. Typically, the probe is excited at wavelengths of at least 400 nm, and in particular embodiments, at about 405 nm. The probe then emits light in the visible range as well, such as at 420 nm, for example.

After incubation, washing, and excitation, the method includes determining whether the probe is internalized by the test cell. A test cell that internalizes the probe is identified as a cell that is susceptible to a polyamine transport system targeting strategy. Any suitable detection strategy may be utilized. In one embodiment, the determining is done by a suitable imaging technique as is known in the art, such as confocal microscopy. In a particular embodiment, the determining is done by any suitable fluorescence detection method known in the art, such as a commercially available plate reader that uses fluorescence. In certain embodiments, the extent to which the probe is internalized is determined quantitatively. In a particular embodiment, commercially available confocal plate imaging system for imaging and taking videos/photos of cells (e.g. Opera Imaging by Perkin Elmer) In one embodiment, the test cell is compared to at least one known standard cell line, such as CHO K1 cell line, which is known to have polyamine transport activity.

In other aspects, the present invention includes methods for monitoring polyamine transport activity in a cancer cell, including a cancer cell known to utilize the polyamine transport system. In one exemplary embodiment, the method comprises contacting the cancer cell with a fluorescent cyano-substituted anthracene probe, such as one or more of compounds 3 and 4, incubating the cancer cell with the probe and optionally washing the cell as described above, exciting the probe at a wavelength of at least 400 nm; and monitoring whether the probe is internalized by the test cell to track the polyamine transport activity of the cell. The monitoring can be done by confocal microscopy such as that referred above, or other suitable imaging techniques.

In certain aspects, the methods described herein may be utilized for high throughput screening methods to screen cancer cells for their polyamine transport activity. Optionally, after contacting the cancer cells with the cyano-substituted probe as described herein, incubating, optionally washing unbound probe from the cells, and exciting the probe with a visible light source, one could quantify the amount of probe internalized by the various cells and rank cell lines accordingly. For example, in one embodiment, the cells lines could be ranked by viewing images, such as those shown in FIGS. 2-3, captured over time for each cell line to quantify how much probe has entered the cell over time. This would then provide a ranking of the cell lines. With this information, one could identify which cancer cell lines are most susceptible and sensitive to PTS-targeting compounds. In some embodiments, the tests compounds are compared to one a known standard cell line, such as the CHO-K1 cell line, which is known to have active polyamine transport activity to determine the extent of PTS activity. Alternatively, rather than utilizing imaging technique, the amount of probe uptaken by the cells may be determined by fluorescence detection methods as are known in the art.

In accordance with yet another aspect, there are provided methods for the use of aldehyde-containing cyano-substituted compounds described herein, such as compounds 7 and 14b. Advantageously, the aldehyde may be utilized to bond, by covalent bonding or otherwise, an amine-containing test compound to aldehyde-containing cyano-substituted compounds as would be readily known by those skilled in the art. Once incubated with a cell under conditions described herein for an effective amount of time, the cell may be imaged to track the cellular uptake and to monitor the cellular uptake or location of a test compound.

Thus, in one embodiment, there is provided a method for monitoring cellular uptake or localization of a test compound having an amine group in a cell comprising: conjugating the test compound to a aldehyde-containing cyano-substituted anthracene probe, the probe comprising a compound selected from the group consisting of compound 7 and 14b; incubating the probe for a time sufficient for the probe to be uptaken by the cell; exciting the probe using a visible light source; and imaging the cell to monitor an extent of cellular uptake or location of the test compound. In one embodiment, the imaging is done by confocal microscopy.

According to a further aspect, provided is a method of screening for chemotherapeutic drug candidates that modulate the uptake of polyamines. The method involves incubating a cell susceptible to polyamine uptake and a fluorescent cyano-substituted anthracene probe for a time sufficient for the probe to be internalized within the cell, wherein said incubating occurs within the presence of a chemotherapy test compound. Upon incubating, the probe is excited using a visible light source, and internalization (uptake) of the probe is determined (such as through microscopy). According to the method, test compounds are identified that block or reduce uptake of the probe, and such test compounds would be considered possible chemotherapeutic agents. Such agents could reduce cancer cell growth or kill cancer cells by starving them of polyamines.

Materials and Methods

Figure 4:
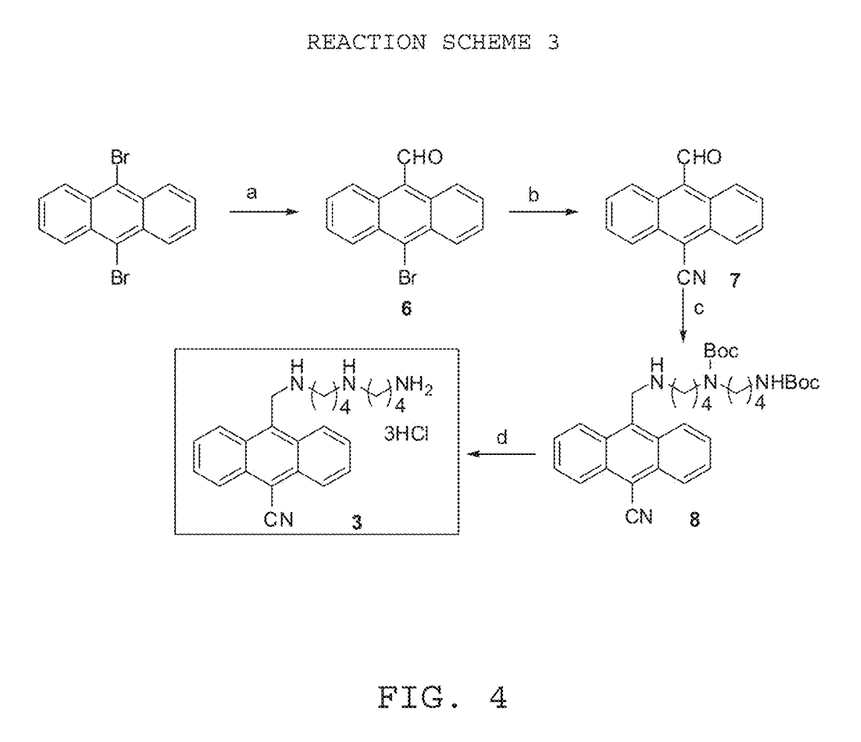
FIG. 4 illustrates a synthetic scheme for producing compound 3 (Reaction Scheme 1), wherein reagents are a) BuLi, DMF, b) Pd(OAc)$_2$/K$_4$[Fe(CN)$_6$], c) H$_2$N(CH$_2$)$_4$N(Boc)(CH$_2$)$_4$NHBoc, NaBH$_4$, and d) 4 N HCl.
Figure 5:
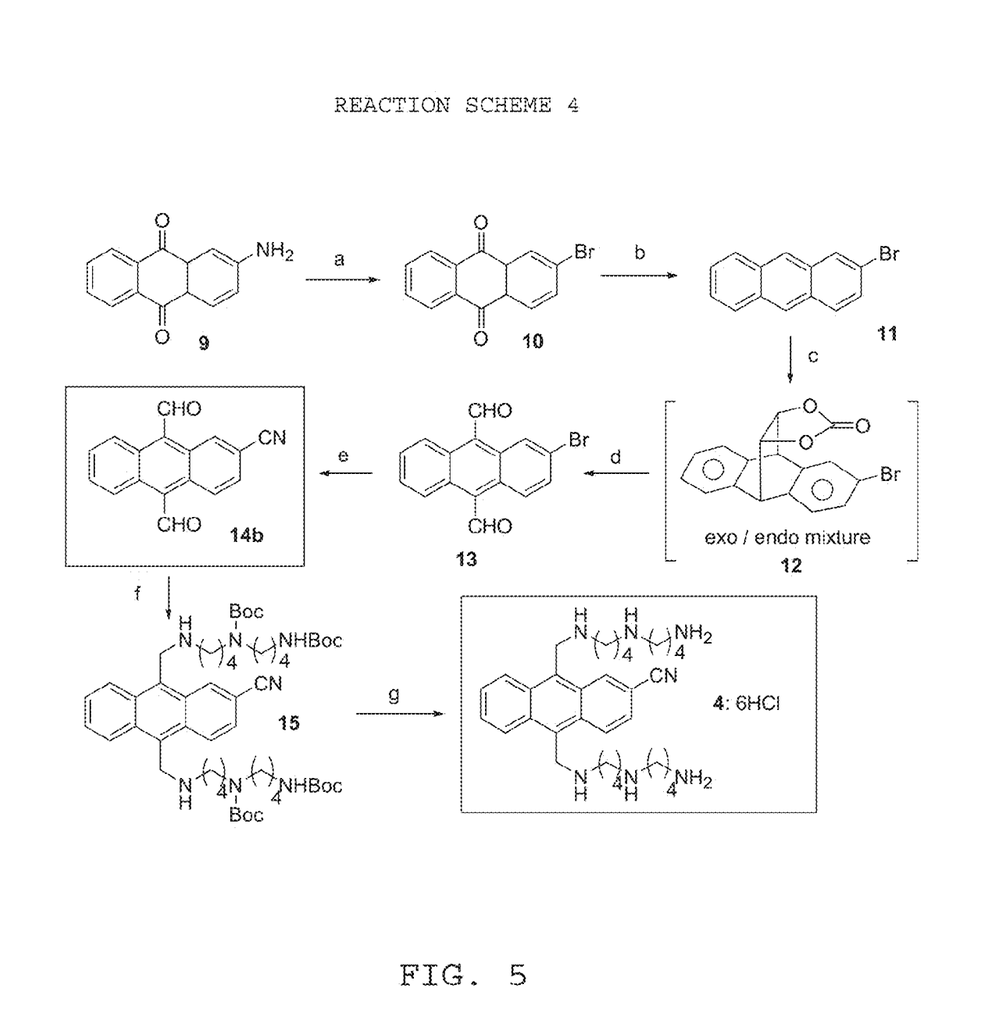
FIG. 5 depicts a synthetic scheme for producing compound 4 (Reaction Scheme 2), wherein reagents employed are (a) CuBr$_2$/t-BuONO; (b) NaBH$_4$, then 3 M HCl; (c) vinylene carbonate, d) KOH/EtOH to give the diol, then Pb(OAc)$_4$; (e) Pd(OAc)$_2$/K$_4$[Fe(CN)$_6$]; (f) H$_2$N(CH$_2$)$_4$N(Boc)(CH$_2$)$_4$NHBoc, NaBH$_4$, and (g) 4 N HCl.

Control compounds 1, 2, and 5 were synthesized previously. REF: (a) "Synthesis and Biological Evaluation of N1-(anthracen-9-ylmethyl)triamines as Molecular Recognition Elements for the Polyamine Transporter," Wang, C.; Delcros, J-G.; Biggerstaff, J.; Phanstiel IV, O. J. Med. Chem. 2003, 46, 2663-2671; (b) A Comparison of Chloroambucil- and Xylene-containing polyamines leads to improved ligands for accessing the polyamine transporter. Navneet Kaur, Jean-Guy Delcros, and Otto Phanstiel IV. J. Med. Chem. 2008, 51, 1393-1401; (c)"N1-Substituent Effects in the Selective Delivery of Polyamine-Conjugates into Cells Containing Active Polyamine Transporters" Gardner, R. A.; Delcros, J-G.; Konate, F.*; Breitbeil III, F.; Martin, B.; Sigman, M.; Huang, M.; Phanstiel IV, O. J. Med. Chem. 2004, 47, 6055-6069.) As shown in FIG. 4, compound 3 was made by multi-step synthesis methods.

10-((4-(4-aminobutylamino)butylamino)methyl)anthracene-9-carbonitrile (3)

The respective diBOC amine 8 (0.15 mmol) was dissolved in EtOH (3 mL) and cooled to 0° C. 4N HCl (6 mL) was added dropwise at 0° C. The solution was stirred at rt overnight. The solution was concentrated under reduced pressure to give a yellow solid 3 in 96% yield. $^1$H NMR (300 MHz, D$_2$O): δ 8.18 (d, 2H), 8.00 (d, 2H), 7.73 (m, 4H), 5.06 (s. 2H), 3.25 (t, 2H), 3.06 (m, 6H), 1.75 (m, 8H). HRMS: theory for $C_{24}H_{30}N_4$.3HCl (M+3H-3Cl): 375.2543. found 375.2553. Anal. calcd for $C_{24}H_{33}N_4Cl_3$.0.2 H$_2$O: C, 59.13; H, 6.91; N, 11.49. Found: C, 59.21; H, 7.01; N, 11.54.

9-Bromo-10-anthracenecarboxaldehyde (6)

To the yellow suspension of 9,10-Dibromoanthracene (2 g, 5.95 mmol) in THF (20 mL) at −90° C., n-BuLi (2.88 mL, 7.18 mmol, 2.5 M in hexane) was added dropwise. Orange solution was observed after 45 min additional stirring. Anhydrous DMF (0.92 mL, 11.9 mmol) was added to the orange solution. The reaction mixture was slowly warmed to room temp and stirred overnight. The reaction mixture was quenched with H$_2$O and extracted with CH$_2$Cl$_2$. The organic layer was washed with 10% aq. Na$_2$CO$_3$ solution (3×50 mL). The CH$_2$Cl$_2$ layer was separated, dried over anhydrous Na$_2$SO$_4$, filtered and removed in vacuo to give yellow solid. The crude product was purified by column chromatography using 30% CH$_2$Cl$_2$/hexane to give 6 in 68% yield. R$_f$=0.3 (30% CH$_2$Cl$_2$/hexane; $^1$H NMR (CDCl$_3$) δ 11.39 (s, 1H), 8.77-8.82 (d, 2H), 8.55-8.60 (d, 2H), 7.56-7.67 (m, 4H). (Ref. de Montigny, Frederic; Argouarch, Gilles; Lapinte, Claude. New route to unsymmetrical 9,10-disubstituted ethynylanthracene derivatives. *Synthesis*, 2006, 2, 293-298.)

9-Cyano-10-anthraldehyde (7)

9-Bromo-10-anthracenecarboxaldehyde (200 mg, 0.7 mmol) was heated with copper (I) cyanide (75.4 mg, 0.84 mmol) and pyridine (3 mL) for 12 hr at 230° C. After cooling, the mixture was washed with dilute NH$_4$OH and ether. The ether extract was washed with water, 1N HCl, again water, dried over anhydrous Na$_2$SO$_4$, filtered and removed in vacuo to give yellow solid, which was purified using column chromatography using 40% CH$_2$Cl$_2$/hexane in 40% yield. $^1$H NMR (CDCl$_3$) δ 11.43 (s, 1H), 8.72-8.77 (d, 2H), 8.44-8.49

(d, 2H), 7.71-7.77 (m, 4H); $^{13}$C NMR (CDCl$_3$): δ 193.4, 160.8, 129.9, 129.4, 129.0, 126.3, 124.4. (Ref. Gore, P. H.; Gupta, S. D.; Obaji, G. A. Anomalous reactions of cyanide with two hindered aromatic aldehydes. *Journal fuer Praktische Chemie* (Leipzig), 1984, 326, 381-384)

Optimized Procedure:

DMAC (N,N-dimethylacetamide) was used as a solvent. As reaction is oxygen sensitive, DMAC was placed in three-necked round-bottomed flask equipped with a three-way stopcock with a vacuum line attached on one side and an ultra-dry N$_2$ filled balloon on the other side. With this setup, the flask headspace could be readily evacuated and nitrogen gas admitted to the evacuated space. Thus, DMAC was kept under a N$_2$ environment. To the three-necked flask Bromoaldehyde 6 (25 mg, 0.088 mmol), Zn(CN)$_2$ (18.5 mg, 0.157 mmol), Pd$_2$(dba)$_3$ (2.09 mg, 0.002 mmol), Zn dust (1 mg, 0.022 mmol) were weighed out and flask was evacuated and N$_2$ gas was allowed to enter the flask via adjustment of the three way stopcock. DMAC (4 mL) was added to the flask via a syringe keeping the flask under vacuum. t-Butyl phosphine (1.77 mg, 0.009 mmol) was added via syringe. The whole assembly was transferred in an oil bath at 80° C. and let the reaction stir at 80° C. for three hours. After monitoring the consumption of 6 by TLC (40% CH$_2$Cl$_2$/Hexane), EtOAc (20 mL) was added to the reaction mixture and crude reaction mixture was washed with saturated solution of K$_2$CO$_3$, and the organic layer was separated and washed with saturated solution of NH$_4$Cl. The EtOAc layer was dried over anhydrous Na$_2$SO$_4$, filtered and concentrated in vacuo to give yellow solid 7 in 89% yield by NMR.

(4-tert-Butoxycarbonylamino-butyl)-{4-[(10-cyano-anthracen-9-ylmethyl)-amino]-butyl}-carbamic acid tert-butyl ester (8): To a stirred solution of N$^1$,N$^5$-di-Boc homospermidine (92 mg, 0.26 mmol) in 25% MeOH/CH$_2$Cl$_2$ (10 mL), was added a solution of 9-Cyano-10-anthraldehyde 7 (49 mg, 0.21 mmol) in 25% MeOH/CH$_2$Cl$_2$ (10 mL) under N$_2$. The mixture was stirred at room temperature overnight until the imine formation was complete (monitored by NMR). The solvent was removed in vacuo, and the solid residue dissolved in 50% MeOH/CH$_2$Cl$_2$ (20 mL) and the solution cooled to 0° C. NaCNBH$_3$ (0.25 mmol) was added in small portions to the solution and the mixture was stirred at rt overnight. The solvent was removed in vacuo, the solid residue dissolved in CH$_2$Cl$_2$ (30 mL) and washed with Na$_2$CO$_3$ solution (10% aq. 3×30 mL). The CH$_2$Cl$_2$ layer was dried over anhydrous Na$_2$SO$_4$, filtered and removed in vacuo to give an oily residue. The oil was purified by flash column chromatography (1.5% MeOH/CH$_2$Cl$_2$) to yield the product as a pale yellow solid (93 mg, 73%), Rf=0.23 (3% MeOH/0.5% NH$_4$OH/CH$_2$Cl$_2$); $^1$H NMR (300 MHz, CDCl$_3$) δ 8.38 (m, 4H), 7.64 (m, 4H), 4.70 (s, 2H), 3.12 (m, 6H), 2.89 (m, 2H), 1.41-1.56 (m, 26H); $^{13}$C NMR: δ 156.0, 155.6, 139.1, 133.1, 129.6, 128.5, 127.0, 126.2, 125.1, 117.5, 79.4, 53.7, 50.6, 46.9, 46.1, 40.4, 28.7, 27.7, 26.1. HRMS (FAB) m/z calcd. for C$_{34}$H$_{46}$N$_4$O$_4$ (M+H)+ 575.3592. found 575.3591. Anal. calcd for C$_{34}$H$_{46}$N$_4$O$_4$·1 H$_2$O: C, 68.89; H, 8.16; N, 9.45. Found: C, 68.77; H, 8.02; N, 9.42.

2-Bromoanthraquinone (10)

Copper (II) bromide (35.0 g, 0.157 mol, 3.76 equiv.) was dissolved in freshly-distilled acetonitrile (200 mL) at room temperature to form an opaque dark-green solution. tert-Butyl nitrite (15 mL, 12.9 g, 0.125 mol, 1.49 equiv.) was added at 0° C. and stirred for 30 minutes at 0° C. 2-Aminoanthraquinone 9 (18.60 g, 0.0834 mol, 1 equiv.) was dissolved in tetrahydrofuran (THF, 300 mL) at room temperature to form an opaque red-brown solution. The 2-aminoanthraquinone 9 solution was quickly added to the copper (II) bromide solution at 0° C. and the solution was stirred for 2 hours at 0° C. with venting of the nitrogen gas by-product every 5 minutes until the bubbling ceased. The consumption of 2-aminoanthraquinone 9 was monitored by thin-layer chromatography (100% CHCl$_3$, R$_f$=0.32). Once the 2-aminoanthraquinone 9 was consumed, the THF and acetonitrile solvents were removed from the mixture via rotary evaporation to give a brown and black solid residue. The solid was rinsed with deionized water to form a suspension. The resulting slurry was vacuum filtered and rinsed with deionized water. The filtrate-receiving flask was changed and the solid was washed with CH$_2$Cl$_2$ through the filter paper, leaving a red-brown solid by-product and forming a yellow-brown solution. The CH$_2$Cl$_2$ was removed from the solution via rotary evaporation, leaving a yellow solid consisting of the product 2-bromoanthraquinone 10 and by-product anthraquinone. The desired product was separated and purified from the unwanted by-product through column chromatography (35% CHCl$_3$/hexane, Rf=0.33 and Rf=0.28 respectively), providing 2-bromoanthraquinone 10 as a light yellow solid (11.2 g; 37%). $^1$H NMR (CDCl3): δ 8.42 (d, 1H), 8.30 (m, 2H), 8.16 (d, 1H), 7.91 (dd, 1H), 7.80 (m, 2H).

2-Bromoanthracene (11): 2-Bromoanthraquinone 10 (8.50 g, 0.0296 mol, 1 equiv) and a 50:50 mixture of isopropyl alcohol and tetrahydrofuran (200 mL) were stirred for 10 minutes at 0° C., forming a yellow suspension. NaBH$_4$ (6.70 g, 0.177 mol, 6.0 equiv.) was added to the suspension at 0° C. The mixture was stirred at 0° C. for three hours, turning red in color. The solution was then warmed to room temperature. Additional NaBH$_4$ (3.35 g, 0.089 mol, 3.0 equiv.) was added to the solution at room temperature and the solution was stirred at room temperature for 12 hours, turning into an orange suspension. Deionized water (10 mL) was added to the solution at room temperature and the solution was stirred at room temperature for an additional 12 hours. The consumption of 2-bromoanthraquinone 10 was monitored by thin-layer chromatography (35% CHCl$_3$/hexane, Rf=0.33). Once the consumption of 2-bromoanthraquinone 10 stopped entirely (it was never fully consumed), the volatiles were removed by rotary evaporation. 3 M HCl was slowly added to the solution until bubbling ceased, then additional 3 M HCl (30 mL) was added. The solution was heated at reflux for 6 hours, turning into an opaque, yellow suspension in the process. The mixture was cooled to room temperature, turning into a transparent solution containing yellow-brown crystals. As much water as possible was removed by rotary evaporation. The contents were then vacuum-filtered and washed using deionized water to remove any water, acid and ionic salt, leaving behind a yellow-brown colored solid. The vacuum-filtration receiving flask was changed and the solid was washed with CH$_2$Cl$_2$ through the filter paper. The CH$_2$Cl$_2$ was removed through rotary evaporation. The remaining solid was purified by column chromatography (100% hexane, R$_f$=0.27), providing 2-bromoanthracene 11 as a white, powdery solid (2.00 g, 26%). $^1$H NMR (CDCl$_3$): δ 8.42 (s, 1H), 8.34 (s, 1H), 8.18 (d, 1H), 8.01 (m, 2H), 7.87 (d, 1H), 7.50 (m, 3H).

2-Bromo-9,10-dihydro-9,10-ethanoanthracene-11,12-diol cyclic carbonate (12): 2-Bromoanthracene 11 (2.05 g, 8.0 mmol, 1 equiv.) and vinylene carbonate (3.68 mL, 5.00 g, 58 mmol, 7.3 equiv.) were heated under reflux with stirring for 18 hours, slowly forming a dark brown solution. The consumption of 11 was monitored by thin-layer chromatography (2% CH$_2$Cl$_2$/hexane, R$_f$=0.31). The mixture underwent rotary evaporation under high vacuum to remove the excess vinylene carbonate, providing the cyclic carbonate intermediate 12 as a light-brown solid (2.74 g, >99%). ¹H NMR (CDCl3): δ 7.52 (dd, 1H), 7.37 (m, 3H), 7.27 (m, 3H), 4.88 (m, 2H), 4.66 (m, 2H).

2-Bromo-9,10-dihydro-9,10-ethanoanthracene-11,12-diol (12a): Solid potassium hydroxide (1.80 g, 32.0 mmol, 4 equiv.), deionized water (30 mL), and absolute ethanol (3.2 mL) were added to the light-brown cyclic carbonate intermediate 12 (2.74 g, 8.0 mmol, 1 equiv.). The solution was stirred at 75° C. for 3 hours. The consumption of the cyclic carbonate intermediate 12 was monitored through thin-layer chromatography (100% $CH_2Cl_2$, $R_f$=0.30). Afterwards, the solvent was removed under reduced pressure to remove the ethanol and roughly half of the water volume. Additional water (60 mL) was added to the solution and the solution was stirred at room temperature for one hour, resulting in the formation of a light-tan solid. The contents were vacuum-filtered and then washed with deionized water. The vacuum-filtration receiving flask was changed and the solid was washed with ethyl acetate through the filter paper. The ethyl acetate was removed through rotary evaporation, leaving a white solid residue. The product was purified through column chromatography (90% $CH_2Cl_2$/ethyl acetate, Rf=0.30 & Rf=0.15), providing two isomers of diol intermediate 12a as a white solid (2.01 g, 79%). ¹H NMR (CDCl3): δ 7.52 (d, 1H), 7.35 (dd, 1H), 7.31 (dd, 2H), 7.25 (d, 1H), 7.17 (dd, 2H), 4.40 (dd, 2H), 4.07 (m, 2H). ¹H NMR (CDCl3): δ 7.45 (d, 1H), 7.34 (dd, 2H), 7.27 (dd, 1H), 7.20 (dd, 2H), 7.16 (d, 1H), 4.35 (dd, 2H), 4.05 (d, 2H).

2-Bromo-9,10-anthracenedialdehyde (13): Diol intermediate 12a (1.58 g, 5.0 mmol, 1 equiv.) was dissolved in anhydrous acetonitrile (100 mL) and heated to reflux with stirring and formed a transparent, light-tan solution. Lead tetraacetate (4.42 g, 10.0 mmol, 2 equiv.) was added portion-wise to the solution over a period of 5 minutes, quickly turning the solution opaque and brown in color. The solution was then stirred at reflux for 4 hours, resulting in the formation of a dark-orange precipitate within the brown solution. The consumption of the diol intermediates were monitored through thin-layer chromatography (80% $CH_2Cl_2$/ethyl acetate, Rf=0.50 & Rf=0.33). After the reaction was complete, the reaction mixture was concentrated via rotary evaporation and gave a burgundy residue. 10% aqueous sodium carbonate (300 mL) was added to the residue, allowing the residue to be suspended in the aqueous solution. The organic contents were extracted from the aqueous layer using dichloromethane. The opaque, yellow organic layer was dried over anhydrous sodium sulfate, filtered, and concentrated to give a yellow-orange solid residue. The residue was purified by column chromatography (20% ethyl acetate/hexane, Rf=0.29), providing 2-bromo-9,10-anthracenedialdehyde 13 as an orange solid (1.23 g, 80%). ¹H NMR (CDCl3): δ 11.43 (s, 1H), 11.42 (s, 1H), 9.03 (s, 1H), 8.72 (m, 2H), 8.66 (d, 1H), 7.75 (m, 3H).

The novelty or improvement on the earlier systems is that even though compounds 1 and 2 are fluorescent, they require excitation in the ultraviolet range (393 nm) and emit in the visible range (410 nm). This requirement is detrimental to biological studies as the UV radiation uses expensive UV lasers, which are costly to maintain and cool during operation. The new compounds 3 and 4 contain a cyano group which extends the compounds' pi system sufficiently such that these compounds are now excited at wavelengths above 400 nm outside the UV range, e.g., 405 nm (blue light) and emit in the visible range, for example, at 420 nm. This improvement in their photophysical properties coupled with their high selectivity in entering cells via the polyamine transport system make these valuable new tools for molecular biologist and cell biologists interested in tracking polyamine uptake phenomena via fluorescence measurements or via confocal microscopy.

While there are numerous biological stains for tracking or labeling cellular organelles, there are no commercial stains or fluorescent agents that specifically enter and traffic through the cell membrane via the polyamine transport system. The novel compounds herein disclosed can be used to study polyamine transport processes in living cells and to track potential therapeutic agents tagged thereon. Accordingly, advantages of the disclosed compounds include their special PTS targeting ability and their desirable photophysical properties.

These compounds, as cellular stains, are further useful added to cancer cells to track how the cancers are trafficking their polyamine growth factors. These agents may also serve as trackable anticancer drug candidates as they are selective for cells with active polyamine transport systems and are cytotoxic at μM concentrations. As shown in FIGS. 2 and 3, the probes are able to discern between PTS-active and PTS-inactive cell lines (blue halo vs dots, respectively).

Prior to the present disclosure there were no commercial stains or fluorescent agents that specifically enter cells and traffic through the polyamine transport system. This is likely a multi-step process and is likely a time dependent phenomenon. We see an initial sequestration of compound 3 into large spheroid bodies followed by escape (or alternative routing) to reach the perinuclear compartment.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

The invention claimed is:

1. A method of screening for cells or cell lines that are susceptible to a polyamine transport system targeting strategy, the method comprising:

contacting at least one test cell with a fluorescent cyano-substituted anthracene probe, wherein the probe is selected from the group consisting of compound 3 and compound 4

-continued

4 incubating the at least one test cell and the probe for a time sufficient for the probe to be internalized within the at least one test cell;
exciting the probe using a visible light source; and
determining whether the probe is internalized by the at least one test cell;
wherein a test cell that internalizes the probe is identified as a cell that is susceptible to a polyamine transport system targeting strategy.

2. The method of claim 1, further comprising washing the at least one test cell to remove unbound probe after the contacting step.

3

3. The method of claim 1, wherein the probe comprises compound 3

4. The method of claim 1, wherein the probe comprises compound 4

4

5. The method of claim 1, wherein the at least one test cell is a known cancerous cell.

6. The method of claim 1, wherein the probe is excited at a wavelength of at least 400 nm.

7. The method of claim 1, wherein the probe has an emission wavelength in the visible light range.

8. The method of claim 7, wherein the probe has an emission wavelength at 420 nm.

9. The method of claim 1, wherein the cells or cell lines are derived from human tissues and are directed to cancer cells, pancreatic beta cells, colonic epithelial cells, white blood cells, macrophages, immune cells, or liver cells, or other human cell types.

10. A method for screening cancer cells for polyamine transport activity comprising:
  contacting a plurality of cells within each of a plurality of distinct cell lines with a fluorescent cyano-substituted anthracene probe selected from the group consisting of compound 3 and compound 4

3

4 incubating the cells and the probe for a time sufficient for the probe to be internalized within the cells;
  exciting the probe using a visible light source; and
  quantifying an amount of internalized probe within each of the cell lines.

11. The method of claim 10, wherein at least one of the cell lines is a cell line having known polyamine transport activity.

12. The method of claim 11, wherein the standard cell line comprises CHO-K1 cell line.

13. The method of claim 10, wherein at least one of the cell lines is a cancer cell line.

14. The method of claim 10, wherein the method is conducted via a high throughput screening process.

15. The method of claim 10, further comprising washing the cells to remove unbound probe after the contacting step.

16. The method of claim 10, wherein the cell lines are derived from human tissue.

17. A method of screening for therapeutic drug candidates that modulate uptake of polyamines in cells, said method comprising
  incubating a cell having active polyamine uptake and a fluorescent cyano-substituted anthracene probe for a time sufficient for the probe to be internalized within the cell, wherein said incubating occurs within the presence of a therapy test compound;
  exciting the probe using a visible light source; and
  determining whether the probe is internalized by the at least one test cell;
  wherein a test compound that modulates uptake of the probe into the cell is identified as a therapeutic drug candidate;
  wherein said probe is compound 3 or 4

18. The method of claim 17, wherein modulation of uptake of the probe comprises increasing or decreasing uptake of the probe.

* * * * *